(12) United States Patent
Barkats

(10) Patent No.: US 9,114,161 B2
(45) Date of Patent: Aug. 25, 2015

(54) WIDESPREAD GENE DELIVERY TO THE RETINA USING SYSTEMIC ADMINISTRATION OF AAV VECTORS

(75) Inventor: Martine Barkats, Charenton le Pont (FR)

(73) Assignees: ASSOCIATION INSTITUT DE MYOLOGIE, Paris (FR); GENETHON, Evry (FR); CENTRE NATIONAL DE LA RECHERCHE SCIENTIFIQUE, Paris Cedex (FR); INSERM (INSTITUT NATIONAL DE LA SANTE ET DE LA RECHERCHE MEDICALE), Paris Cedex (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 13/388,083

(22) PCT Filed: Jul. 30, 2010

(86) PCT No.: PCT/EP2010/061165
§ 371 (c)(1),
(2), (4) Date: Feb. 24, 2012

(87) PCT Pub. No.: WO2011/012724
PCT Pub. Date: Feb. 3, 2011

(65) Prior Publication Data
US 2012/0141422 A1    Jun. 7, 2012

(30) Foreign Application Priority Data
Jul. 31, 2009  (EP) .................................... 09305722

(51) Int. Cl.
*A61K 48/00* (2006.01)
*C12N 15/861* (2006.01)
*A61P 27/02* (2006.01)

(52) U.S. Cl.
CPC ... *A61K 48/0075* (2013.01); *C12N 2750/14143* (2013.01)

(58) Field of Classification Search
CPC ......................................................... G01N 35/02
See application file for complete search history.

(56) References Cited

FOREIGN PATENT DOCUMENTS
WO    WO 2009/046059    4/2009

OTHER PUBLICATIONS

Lei et al. (Molecular Vision. Published online Jul. 17, 2009; 15: 1374-1382).*
Yang et al (J. Virol. 2002; 76: 7651-7660).*
Steuer et al (Investigative Ophthalmology & Visual Science. Mar. 2005; 46(3): 1047-1053).*
Duque et al. (Molecular Therapy. Jul. 2009 [published online Apr. 14, 2009]; 17(7): 1187-1196).*
Zhu et al. (Investigative Ophthalmology & Visual Science. 2002; 43(9): 3075-3080).*
Bostick et al. (Gene Therapy. 2007; 14: 1605-1609).*
Glushakova, L. G. et al. "495. Transfer of LEDGF to the Mouse Retina Via Systemic AAV Vector Administration" *Molecular Therapy*, Jan. 1, 2006, p. S192, vol. 13, Supp. 1.
Bostick, B. et al. "Systemic AAV-9 transduction in mice is influenced by animal age but not by the route of administration" *Gene Therapy*, 2007, pp. 1605-1609, vol. 14.
Natkunarajah, M. et al. "Assessment of ocular transduction using single-stranded and self-complementary recombinant adeno-associated virus serotype 2/8" *Gene Therapy*, 2008, pp. 463-467, vol. 15, No. 6.
Written Opinion in International Application No. PCT/EP2010/061165, Sep. 23, 2010, pp. 1-5.
Allocca, M. et al. "Novel Adeno-Associated Virus Serotypes Efficiently Transduce Murine Photoreceptors" *Journal of Virology*, Oct. 2007, pp. 11372-11380, vol. 81, No. 20.

* cited by examiner

*Primary Examiner* — Scott Long
(74) *Attorney, Agent, or Firm* — Saliwanchik, Lloyd & Eisenschenk

(57) ABSTRACT

The present invention relates to compositions and methods, in particular to methods based on systemic administration of scAAV, for delivering genes to cells of the retina of mammals, and in particular to photoreceptor cells, ganglion cells, glial cells, inner nuclear layer cells or cells of the retinal pigmented epithelium.

25 Claims, 5 Drawing Sheets

Figure 1:
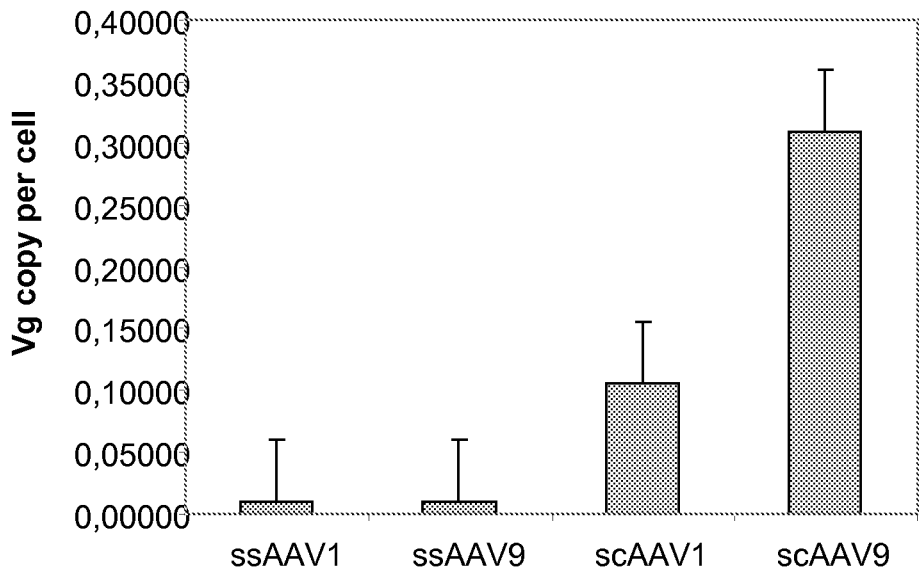
Figure 1:
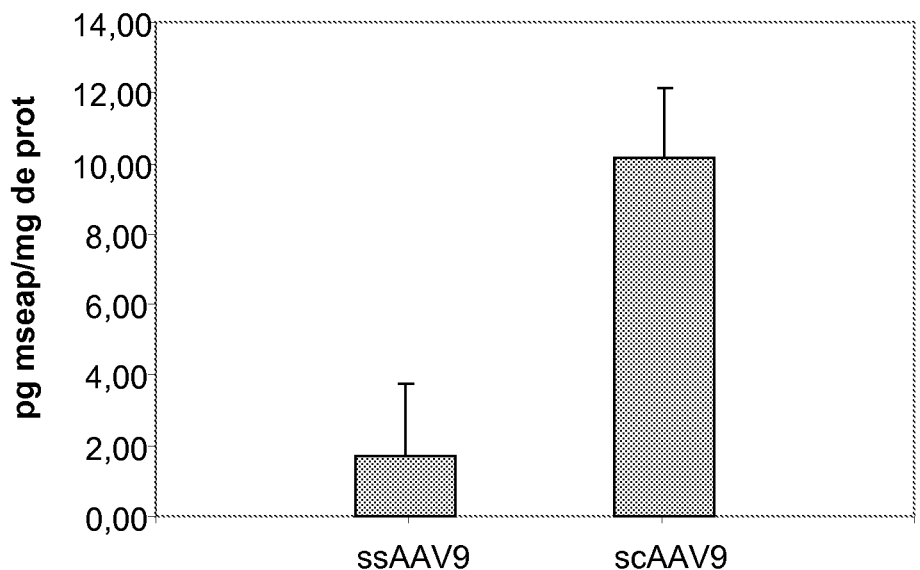

SEQUENCE LISTING

```
<160> NUMBER OF SEQ ID NOS: 6

<210> SEQ ID NO 1
<211> LENGTH: 22
<212> TYPE: DNA
```

```
<213> ORGANISM: artificial
<220> FEATURE:
<223> OTHER INFORMATION: AAV ITR forward primer

<400> SEQUENCE: 1
ctccatcact aggggttcct tg                                           22

<210> SEQ ID NO 2
<211> LENGTH: 18
<212> TYPE: DNA
<213> ORGANISM: artificial
<220> FEATURE:
<223> OTHER INFORMATION: AAV ITR reverse primer

<400> SEQUENCE: 2
gtagataagt agcatggc                                                18

<210> SEQ ID NO 3
<211> LENGTH: 20
<212> TYPE: DNA
<213> ORGANISM: artificial
<220> FEATURE:
<223> OTHER INFORMATION: MGB probe

<400> SEQUENCE: 3
tagttaatga ttaacccaav                                              20

<210> SEQ ID NO 4
<211> LENGTH: 21
<212> TYPE: DNA
<213> ORGANISM: artificial
<220> FEATURE:
<223> OTHER INFORMATION: Titin forward primer

<400> SEQUENCE: 4
aaaacgagca gtgacgtgag c                                            21

<210> SEQ ID NO 5
<211> LENGTH: 20
<212> TYPE: DNA
<213> ORGANISM: artificial
<220> FEATURE:
<223> OTHER INFORMATION: Titin reverse primer

<400> SEQUENCE: 5
ttcagtcatg ctgctagcgc                                              20

<210> SEQ ID NO 6
<211> LENGTH: 25
<212> TYPE: DNA
<213> ORGANISM: artificial
<220> FEATURE:
<223> OTHER INFORMATION: Vic/TAMRA probe

<400> SEQUENCE: 6
tgcacggaag cgtctcgtct cagtc                                        25
```

WIDESPREAD GENE DELIVERY TO THE RETINA USING SYSTEMIC ADMINISTRATION OF AAV VECTORS

CROSS-REFERENCE TO RELATED APPLICATION

This application is the U.S. national stage application of International Patent Application No. PCT/EP2010/061165, filed Jul. 30, 2010.

The Sequence Listing for this application is labeled "SeqList.txt" which was created on Jan. 27, 2012 and is 2 KB. The entire contents of the sequence listing is incorporated herein by reference in its entirety.

The present invention relates to compositions and methods for delivering genes to cells of the retina in mammals. The invention also relates to methods of treating disorders of the eye, in particular disorders of the retina, in mammals by expression of therapeutic genes. The invention stems from the unexpected discovery that systemic administration of double stranded AAV vectors leads to a massive and widespread infection of the retina cells despite of the blood-retina-barrier. The invention may be used in any mammal, including human subjects.

INTRODUCTION

The retina is a light sensitive layer of the inner part of the eye. It is formed by several cell types, including the photoreceptor cells (rods and cones) and the ganglion cells. The photoreceptors receive light and transform it into signals transported to the brain through the optic nerve. A small proportion of the retina's ganglion cells (about 2%) are also photosensitive and transmit information to the brain through the retinohypothalamic tract. These cells have a role in the adjustment of the pupil size and in the control of circadian rhythms. A pigmented cell layer (hexagonal cells), located outside the neurosensory retina and attached to the underlying choroid, corresponds to the retinal pigment epithelium (RPE). The RPE is involved in the phagocytosis of the outer segment of the photoreceptor cells. It is also involved in the vitamin A cycle (isomerization of trans-retinol to 11-cis retinal).

A large majority of the genes involved in retinal dystrophies (such as AIPL1, CRB1, CRX, GUCY2D, RPE65, LCA5 et RPGRIP1 in Leber congenital amaurosis (LCA) (il a plus de 56 gènes associés pour la rétinite pigmentaire je ne peux pas aller verifier pour chacun . . . supprimons donc cette maladie puisque je ne saurais être exhaustive et laissons à titre d'exemple l'amaurose de Leber) are expressed in the RPE or the photoreceptors. The targeting of the photoreceptors and/or RPE is thus essential for effective gene therapies of retinal diseases, although other cell types such as the bipolar cells and the Müller cells (the principal glial cell type of the retina) are also valuable target cells (see below).

Transgene delivery to retinal cells in animal models usually needs subretinal or intravitreal injections of viral vectors. This procedure is relatively efficient to direct transgene expression into photoreceptor or RPE cells.

However, subretinal injections of either adeno-associated vectors (rAAV) or lentiviral vectors cause detachment of the retina at the site of injection, and can lead to subsequent localized trauma inducing retinal thinning and cell destruction, in particular in affected animals (Le Meur et al., 2007; Pang J. et al., 2008, Cheng L et al., Retina 2005). Moreover, subretinal vector injections direct transgene expression only in the injected areas of the treated eye with a limited diffusion to non-treated eyes; typically only 20-30% of the retina can be transduced in AAV-injected neonatal mice although diffusion of the vector is usually experimenter dependent.

Although intravitreal rAAV injection is efficient to direct transgene expression into retinal cells, the invasive nature of this direct administration route could represent risks for the patient. No transgene expression could be seen in eyes that received intravitreal injection of lentiviral vectors.

An alternative efficient and non-invasive method for gene transfer to the retina consists in systemic delivery of viral gene vectors. This would be an optimal strategy for clinical applications, but it is hampered by the tight junctions of the blood-retina barrier that precludes the entry of viral vectors from the bloodstream to the subretinal space, especially in adults.

Recombinant AAV are among the most powerful gene delivery tools for gene transfer into the retina. They are not pathogenic for humans, display low immunogenicity, and can achieve high level and stable transgene expression in post-mitotic cells.

However, given the drawbacks associated with intravitreal or subretinal injections, alternative administration methods for gene therapy are needed. Daly et al. (PNAS, 1999) and Bostick et al. (Gene Therapy, 2007) intravenously injected conventional, single stranded, AAV vectors encoding the human GUSB (β-glucuronidase) gene or the alkaline phosphatase (AP) reporter gene, respectively, in newborn mice. The transgene products were found in many organs, including the retina. However, the retina was transduced only in newborn mice, in which the blood retina barrier is immature.

In the above mentioned studies of Daly et al. (1999) and Bostick et al. (2007), no information was provided regarding transgene expression levels (DNA or RNA) in the retina cells. Since both AP and GUSB are secreted enzymes, their presence within the retina could be due to their transport as circulating enzymes rather than to their expression within the retinal cells.

There is, therefore, a need to develop alternative strategies allowing efficient targeting of the different retinal layers, in particular of RPE, photoreceptor and retinal ganglion cells, with gene transfer vectors. Furthermore, there is no efficient method to date for efficient targeting of inner cells of the retina such as the bipolar cells or the Müller cells (the principal glial cell type of the retina). However, gene transfer into bipolar cells could also have a great therapeutic potential as demonstrated by restoration of the vision in blind mice following expression of light-activated channels in bipolar cells (Lagali et al., Nature Neuroscience, 2008, vol. 11 (6), p. 667-675). Similarly, Müller cells (the principal glial cell type of the retina) could also be highly valuable target cells since disease-causative genes (such as CRB1 in Leber Congenital Amaurosis) were found to be expressed not only in photoreceptors, but also in these specific glial cells. A method for providing gene delivery into bipolar and Müller cells would thus be highly advantageous.

The results presented below demonstrate that recombinant self-complementary double stranded AAV vectors (scAAV), in particular of serotype 9, enables transgene delivery to the retina after intravenous administration in adult mice. Both secreted (mSEAP, murine secreted alkaline phosphatase) and non secreted (GFP, green fluorescent protein) proteins were found to be expressed in the retina, suggesting the efficient transduction of the adult retina cells. Transgene expression in the transduced retina cells was further confirmed by detection of the transgene DNA in the retina using quantitative PCR. This study shows, for the first time, that it is possible to efficiently transfer genes of interest to the retina cells after a single systemic administration (in particular by intravenous injection) of a scAAV vector (in particular a scAAV9 vector) comprising said gene of interest, achieving broad transgene expression in the retina. These findings therefore offer new avenues for the treatment of eye diseases, and more particularly for the treatment of retina disorders.

SUMMARY OF THE INVENTION

An object of the invention relates to a double stranded self-complementary AAV (scAAV) vector comprising a therapeutic gene of interest, for use in the treatment of a disorder of the eye, preferably a disorder of the retina, by systemic administration of said scAAV vector to said subject.

The invention also relates to a scAAV vector as described above, for use in the treatment of the disorder by delivery of the therapeutic gene to retinal cells such as photoreceptor cells, ganglion cells, glial cells (in particular Müller cells), inner nuclear layer (INL) cells (including bipolar cells, horizontal cells, and amacrine cells), or cells of the retinal pigmented epithelium (RPE). Systemic injection of a scAAV vector can also direct gene transfer to the ciliary bodies. This represents a particularly valuable method for secreting a therapeutic protein (such as anti-VEGF factors) into the eye.

The invention further relates to a scAAV vector as described above, for producing a therapeutic protein or RNA into, or from, cells of the retina. The production of the therapeutic protein or RNA can take place in retinal cells such photoreceptor cells, ganglion cells, glial cells (in particular Müller cells), inner nuclear layer (INL) cells (including bipolar cells, horizontal cells, and amacrine cells), or cells of the retinal pigmented epithelium (RPE), for example.

The invention also relates to a scAAV vector as described above, administered by intraperitoneal (i.p.), intramuscular (i.m.), intra-arterial or intravenous (i.v.) injection, preferably i.v. injection.

Furthermore, the invention relates to a scAAV vector as described above, wherein said scAAV vector is a human serotype AAV vector, preferably selected from serotypes 6, 8 and 9, most preferably serotype 9.

An scAAV9 is a representative scAAV which can be used according to the invention. Therefore, the invention also relates to a scAAV vector as described above, wherein said scAAV vector comprises an AAV9-capsid.

The invention also relates to a scAAV vector as described above, wherein said scAAV vector is a pseudotyped scAAV vector, preferably a scAAV2/9 vector.

The invention further relates to a scAAV vector as described above, wherein the scAAV vector (for example a scAAV9 or scAAV2/9 vector) comprises a replication defective scAAV genome lacking functional Rep and Cap coding viral sequences.

The invention also relates to a scAAV vector as described above, wherein the gene encodes a therapeutic RNA, or a therapeutic protein known to be mutated or deficient in pathological disorders of the eye, preferably in pathological disorders of the retina, in particular in pathological disorders involving retinal cells such as photoreceptor cells, ganglion cells, glial cells (in particular Müller cells), inner nuclear layer (INL) cells (including bipolar cells, horizontal cells, and amacrine cells), or cells of the retinal pigmented epithelium (RPE).

The invention also relates to a scAAV vector as described above, for the treatment of a retinal disorder selected from both inherited (for example Leber's congenital amaurosis) and sporadic (for example diabetic retinopathy) eye disorders, including in particular disorders of the choroid and retina. Representative disorders include Retinitis pigmentosa, Macular degeneration, Cone-rod dystrophy, Retinal detachment, hypertensive retinopathy, Retinoblastoma, Leber's congenital amaurosis, Macular edema, Birdshot chorioretinopathy, Vitelliform macular dystrophy, Glaucoma, disorders of the vitreous body and globe, etc. The invention also provides means for treating some other disorders of the eye by gene transfer of a secreted therapeutic protein, including disorders of sclera, cornea, iris and ciliary body, disorders of optic nerve and visual pathways (ex: Leber's hereditary optic neuropathy), disorders of ocular muscles, etc.

Another object of the invention relates to the use of a scAAV vector comprising a therapeutic gene of interest for the manufacture of a medicament for the treatment of a disorder of the eye, in particular a disorder of the retina, by systemic administration of said scAAV vector to said subject.

The invention further relates to a method of delivering a gene across the blood retinal barrier, comprising the step of administering by systemic route a scAAV vector comprising said gene to a mammal in need thereof.

A further object of the invention relates to a method of delivering a gene, in particular a therapeutic gene, to cells of the retina in a mammal in need thereof, the method comprising administering to the mammal by systemic route a scAAV vector comprising said gene. Said administration allows infection of cells of the retina, in particular of photoreceptor cells, ganglion cells, glial cells (in particular Müller cells), inner nuclear layer (INL) cells (including bipolar cells, horizontal cells, and amacrine cells), or cells of the retinal pigmented epithelium (RPE) by said scAAV vector and thereby delivery of said gene, and expressed protein, into said cells of the retina.

Another object of the invention relates to a method of delivering a gene, in particular a therapeutic gene, to the ciliary bodies of the eye or to the optic nerve, in mammals in need thereof, the method comprising administering to the mammal by systemic route a scAAV vector comprising said gene. The invention thus also relates to a scAAV vector as described in further details below, for use in the treatment of a disorder of the eye by systemic administration of said scAAV vector to a subject in need thereof, thereby infecting cells of the ciliary body or the optic nerve.

The invention also relates to a method of gene therapy across the blood retina barrier in a mammalian subject, the method comprising the systemic administration of a scAAV vector to the subject. In particular, a scAAV9 (or scAAV2/9) vector, but not only, can be used.

A further object of this invention is a method of genetically modifying cells in the eye, more particularly in the retina, in particular photoreceptor cells, ganglion cells, glial cells (in particular Müller cells), inner nuclear layer (INL) cells (including bipolar cells, horizontal cells, and amacrine cells), or cells of the retinal pigmented epithelium (RPE), in a mammalian subject, the method comprising systemically administering scAAV vectors to the subject. In a particular embodiment, the modified cells of the eye are ciliary body cells.

The invention also resides in a method of gene delivery to the retina of a subject, the method comprising systemically administering to the subject a scAAV vector comprising said gene. Illustrative examples of retina cells which can be targeted by the scAAV vector of the invention include photoreceptor cells, ganglion cells, glial cells (in particular Müller cells), inner nuclear layer (INL) cells (including bipolar cells, horizontal cells, and amacrine cells), or cells of the retinal pigmented epithelium (RPE), or cells of the ciliary bodies.

Further objects and applications of the invention are provided in the below detailed description.

LEGEND TO THE FIGURES

FIG. 1. mSEAP Expression in Eye Tissue Samples From I.V. AAV-mSEAP Injected Adult Mice.

(A) Vector genome copy number in eye tissue samples from mice injected into the tail vein with ssAAV1, ssAAV9, scAAV1, and scAAV9. In each group, 2 mice were injected with 1×10e12 vg and 1 mouse with 3×10e11 vg. Values are means+/−standard errors of the mean (SEM).

(B) mSEAP activity number in eye tissue samples from mice injected into the tail vein with ssAAV9 and scAAV9. In each group, 2 mice were injected with 1×10e12 vg and 1 mouse with 3×10e11 vg. Values are means+/−standard errors of the mean (SEM).

Figure 2:
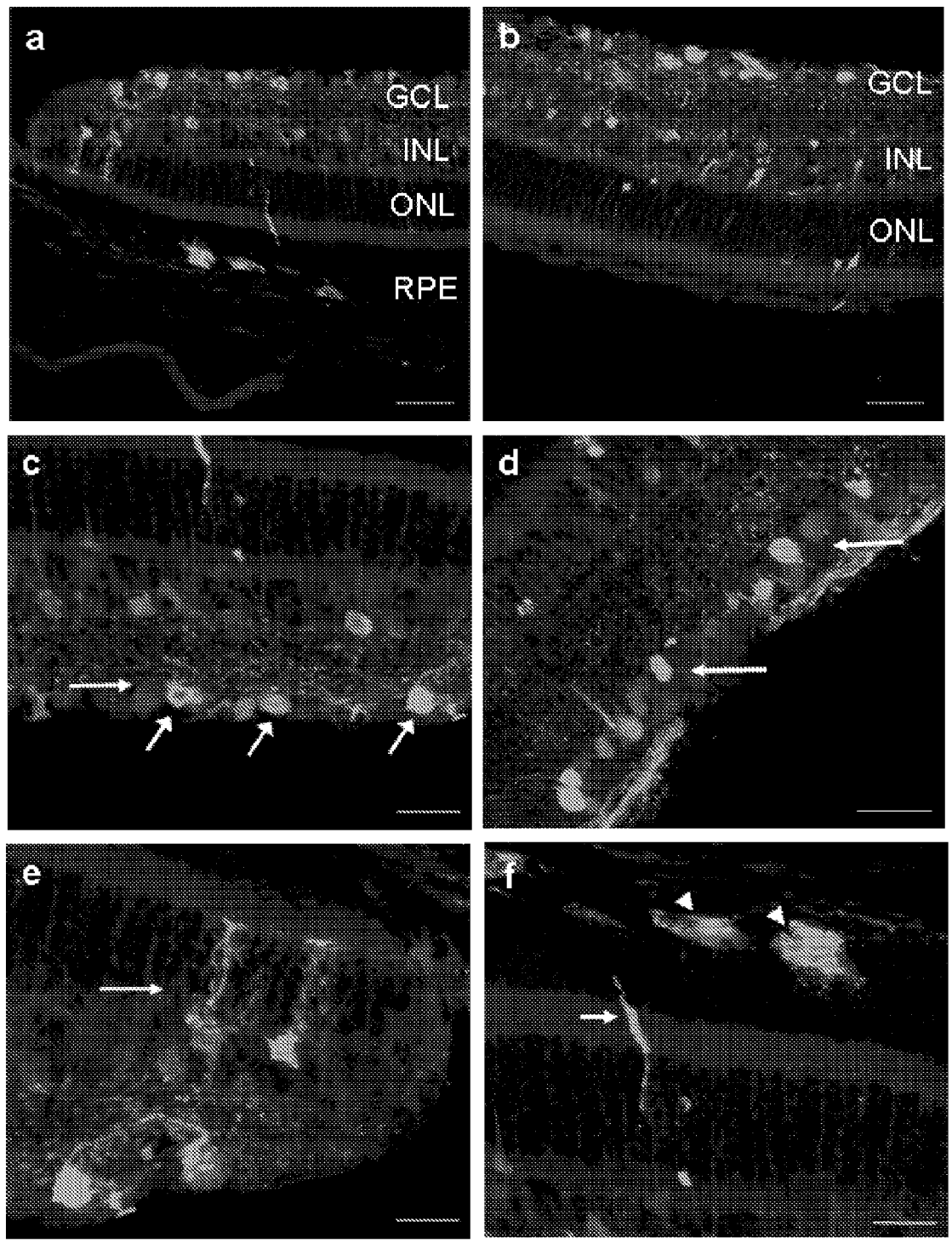

FIG. 2. Representative Cross-Sections of Retina From Adult Mice IV Injected With a scAAV9-GFP Vector -I-

Retinal sections treated for GFP immunofluorescence 4 weeks after IV injection of $2 \times 10^{12}$ vg of scAAV9 vectors showed transduction of several retina layers (a-b) including (a-d) ganglion cells (GCL, arrows), (a,b,e) the inner nuclear layer (INL, arrows), (f) rare photoreceptor cells (arrow) and (a,f) retinal pigmented epithelial cells (RPE, arrowheads). GCL: ganglion cell layer; INL: inner nuclear layer; ONL: outer nuclear layer; RPE: retinal pigmented epithelium.

Figure 3:
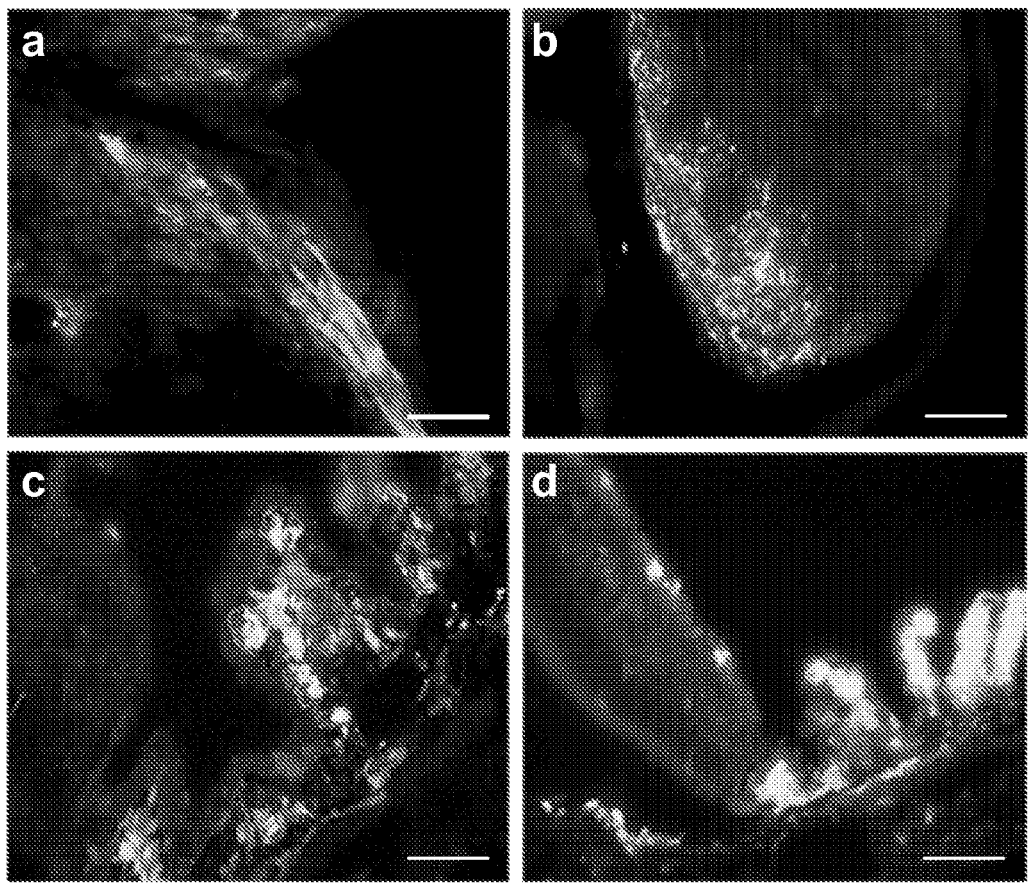

FIG. 3. Representative Cross-Sections of Retina From Adult Mice IV Injected With a scAAV9-GFP Vector -II- GFP immunofluorescence analysis performed 4 weeks after IV injection of $2 \times 10^{12}$ vg of scAAV9 vectors showed an intense GFP staining of (a, b) retinal nerve fibers in the optic nerve (originating from the GCL) and of (c,d) the ciliary bodies. Scale bars 50 µm.

Figure 4:
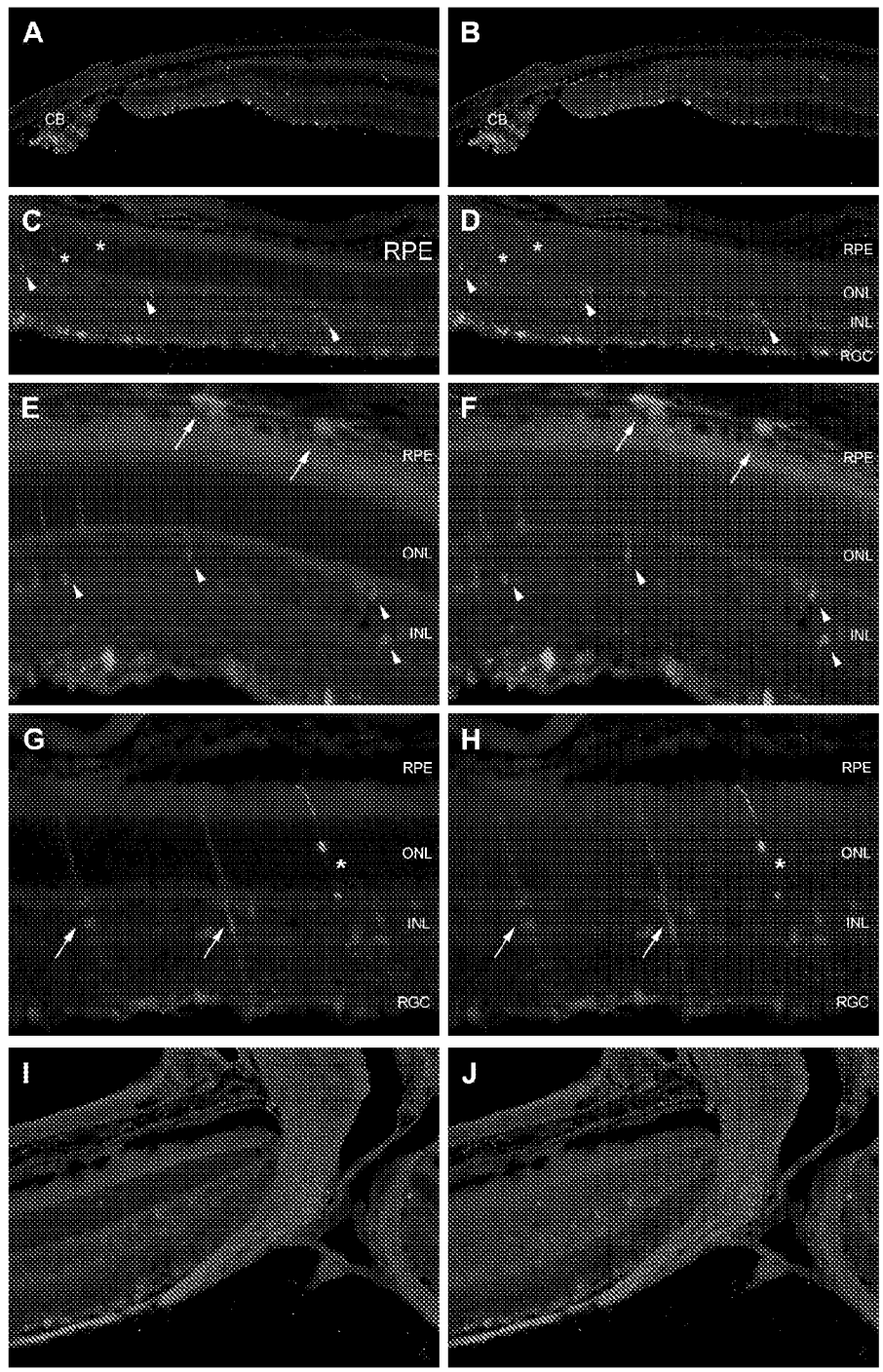

FIG. 4. GFP expression in the retina after intravenous delivery of scAAV9 in adult mice.

GFP immunofluorescence (A, C, E, G), and the same view counterstained with the Dapi nuclear marker (B, D, F, H) of mice 4 weeks after tail vein delivery of $2 \cdot 10^{12}$ vg of scAAV9-CMV-GFP at 8 weeks of age. GFP expression was present in the ciliary bodies (CB in A and B) and in numerous cells of the RGC layer (A-D, G, H), as well as in different cell types of the INL, including cells with the morphology of bipolar cells (arrowheads in C-F) and of Müller cells (arrows in G and H). Sparse photoreceptors (asterisks in C, D, G and H) and RPE cells (arrows in E and F) were also detected. (I, J) GFP positive retinal nerve fibers in the optic nerve (originating from the GCL). RPE: retinal pigment epithelium; ONL: outer nuclear layer; INL: inner nuclear layer; RGC: retinal ganglion cell layer.

Figure 5:
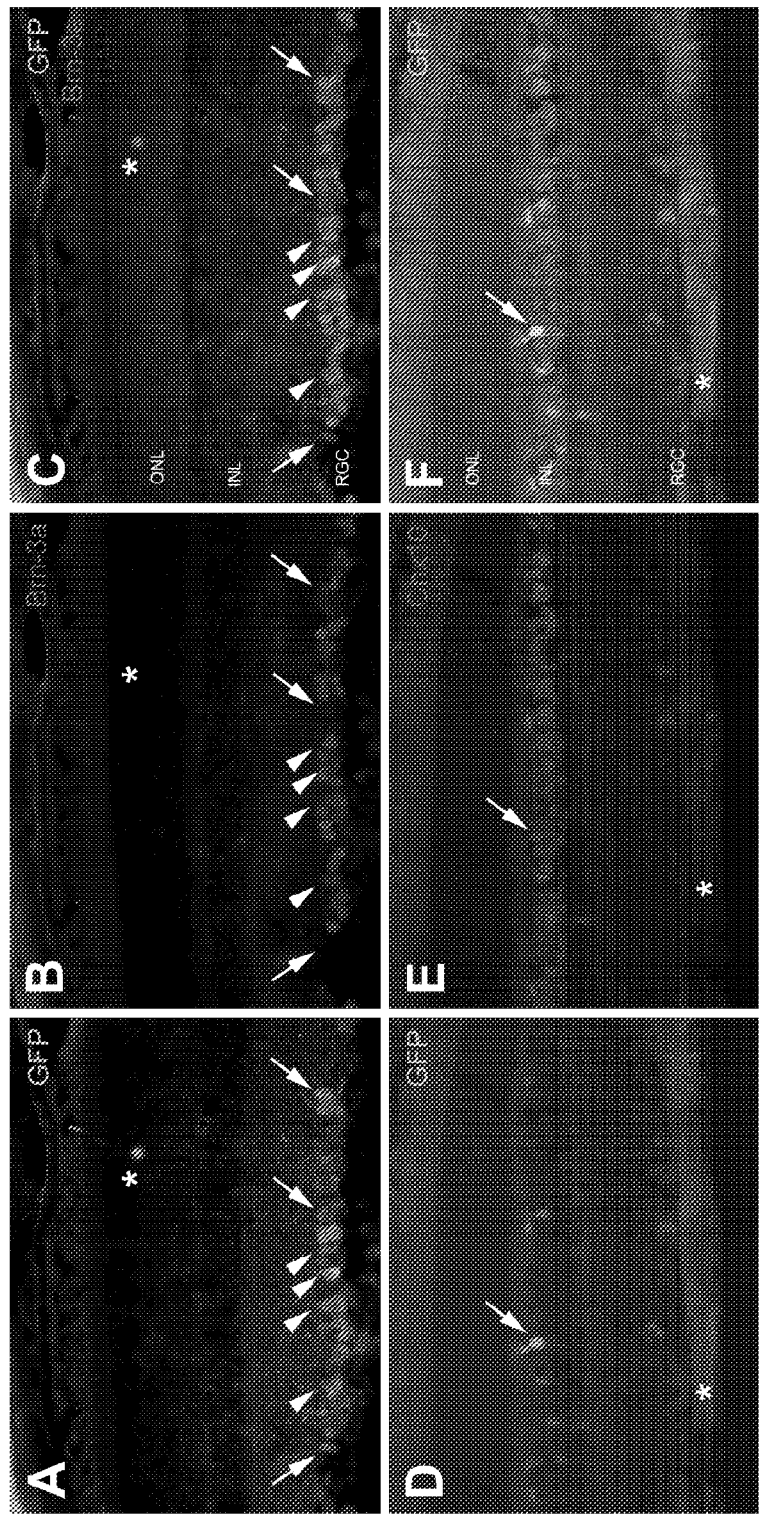

FIG. 5. Systemic scAAV9 injection mediates gene transfer to RCG and bipolar cells in the adult mouse retina (A-C) GFP/Brn-3a (RCG-specific marker) and (D-F) GFP/Chx10 (bipolar cells specific marker) double-immunostaining of the retina revealed efficient transduction of ganglion and bipolar cells. Double labeling was performed on transversal cryostat sections of the retina taken 4 weeks after tail vein injection of scAAV-CMV-GFP vector in adult mice ($2.10^{12}$ vg per mouse). In (A-C): arrowheads indicate double-labeled RGC and arrows indicate cells expressing only GFP; a transduced photoreceptor is highlighted by an asterisk. In (D-F): the arrow points out a Chx10 positive bipolar cell expressing high level of GFP; the retinal nerve fiber layer (asterisk) appears GFP positive due to the transduction of upstream RGC. ONL: outer nuclear layer; INL: inner nuclear layer; RGC: retinal ganglion cell layer.

DETAILED DESCRIPTION OF THE INVENTION

Widespread gene delivery to the retina is an important challenge for the treatment of diseases of the eye, in particular of diseases of the retina such as retinal dystrophies, including Leber congenital amaurosis (LCA) or retinitis pigmentosa (RP). Here, we describe a new method for eye gene transfer based on systemic administration of recombinant self-complementary double-stranded AAV vectors (scAAV).

The inventors have demonstrated that a single intravenous (IV) injection of recombinant scAAV vectors in the adult mouse can achieve widespread transgene expression in both eyes, including the different layers of retina, the ciliary bodies, the nerve fiber layer, and the choroid. This was first observed at the DNA and protein level following IV injection of scAAV vectors encoding the murine secreted alkaline phosphatase reporter gene (mSEAP). The superiority of scAAV vectors for IV gene transfer into the eyes of adult mice was then confirmed on eye histological sections after IV injection of scAAVs expressing the green fluorescent protein (GFP) and immunodetection of the transgene product. The different laminae of the retina were found to be transduced (although with different efficiencies). These transduced layers included the choroid, the RPE, the photoreceptor and outer nuclear layers (rods/cones), the outer plexiform and inner nuclear layers (bipolar, horizontal and amacrine cells), the inner plexiform and ganglion cell layers (ganglion cells), the nerve fiber layer (axonal fibers from the ganglion cells), the innermost layer (Müller cells). The ciliary bodies were also found to be highly transduced.

Importantly, this procedure of gene delivery did not cause any damage to the retina such as retinal detachment or thinning. The inventors thus demonstrate for the first time that non-invasive systemic delivery of scAAV vectors can direct widespread transduction of retinal cells in adult animals.

This unprecedented systemic AAV-mediated gene transfer to the adult retina offers promising applications for gene therapy of a large majority of eye diseases, preferably of diseases of the retina.

AAV Vectors

Within the context of the present invention, the term "AAV vector" designates any vector which comprises or derives from components of AAV and is suitable to infect mammalian cells, preferably human cells. The term AAV vector typically designates an AAV type viral particle (or virion) comprising at least a nucleic acid molecule encoding a therapeutic protein. As will be discussed below, the AAV may be derived from various serotypes, including combinations of serotypes (i.e., "pseudotyped" AAV) or from various genomes. In addition, the AAV vector may be replication defective and/or targeted.

Adeno-associated virus (AAV) is a dependent parvovirus, of approximately twenty nanometers in size. Like other parvoviruses, AAV is a single-stranded, non-enveloped DNA virus, having a genome of about 5000 nucleotides in length, containing two open reading frames. The left-hand open reading frame codes for the proteins responsible for replication (Rep), while the right-hand open reading frame encodes the structural proteins of the capsid (Cap). The open reading frames are flanked by two ITR sequences, which serve as the origin of replication of the viral genome. Furthermore, the genome also contains a packaging sequence, allowing packaging of the viral genome into an AAV capsid.

AAV requires co-helper functions (which may be provided e.g. by an adenovirus, or by suitable packaging cells or helper plasmids) to undergo a productive infection in cultured cells. In the absence of such helper functions, the AAV virions essentially enter the cells, migrate to the nucleus as a single-stranded DNA molecule, and integrate into the cell genomes.

AAV has a broad host range for infectivity, including human cells, is ubiquitous in humans, and is completely non-pathogenic.

AAV vectors have been designed, produced and used to mediate gene delivery in human subjects, including for therapeutic purposes. Clinical trials are presently ongoing in various countries using AAV vectors. Typically, AAV vectors for use in gene transfer comprise a replication defective AAV genome lacking functional Rep and Cap coding viral sequences. Such replication defective AAV vectors more preferably lack most or all of the Rep and Cap coding sequences, and essentially retain one or two AAV ITR sequences and a packaging sequence.

Methods of producing such AAV vectors have been disclosed in the literature, including using packaging cells, auxiliary viruses or plasmids, and/or baculovirus systems (Samulski et al., (1989) J. Virology 63, 3822; Xiao et al., (1998) J. Virology 72, 2224; Inoue et al., (1998) J. Virol. 72, 7024; WO98/22607; WO2005/072364). It should be noted that several of these methods relates to helper-free AAV production, which is a preferred production method within the scope of the present invention. Methods of producing pseudotyped AAV vectors have also been reported (e.g., WO00/28004), as well as various modifications or formulations of AAV vectors, to reduce their immunogenicity upon in vivo administration (see e.g., WO01/23001; WO00/73316; WO04/112727; WO05/005610; WO99/06562).

The present invention implements double-stranded AAV vectors, i.e. the AAV genome is a double-stranded, self complementary (scAAV) nucleic acid (McCarty et al., Gene Therapy, 2003). ScAAV vectors are generated by deleting the terminal resolution site (trs) from one of the AAV terminal repeats. These modified vectors, whose replicating genome is half the length of the wild type have the tendency to package DNA dimers (McCarty et al., Gene Therapy, 2003). Briefly, during the replication cycle of AAV, Rep endonuclease nicks the trs to initiate a second DNA replication process generating monomeric genomes. Dimeric genomes of scAAV are generated when Rep fails to nick the trs (McCarty, Molecular Therapy 2008). Replication continues through the ITR to generate a dimeric template which initiates a new round of DNA synthesis, producing a dimeric single-strand genome (dimeric inverted repeat genomes). Both strands are thus packaged into the AAV virion as a single molecule. The two halves of the single-strand DNA molecule can then fold and base pair to form a dsDNA molecule. The above mentioned articles of McCarty et al. describe in details the production process of a scAAV and may be followed to obtain a vector according to the invention.

AAV vectors may be prepared or derived from various serotypes of AAVs, which may be even mixed together or with other types of viruses to produce chimeric (e.g. pseudotyped) AAV viruses. In a particular embodiment, the scAAV vector for use in the present invention is derived from a human AAV virus. Such a human AAV (capsid and ITR) may be derived from any known serotype, e.g. from any one of serotypes 1-11, preferably from AAV2, AAV4, AAV6, AAV8 and AAV9, more preferably from AAV6, AAV8 and AAV9, even more preferably from AAV9. Specific examples of such AAV vectors are vectors comprising an AAV2-derived genome (a nucleic acid molecule comprising an AAV2-derived ITR and an AAV2-derived packaging sequence, operatively linked to a nucleic acid encoding a therapeutic protein, preferably two AAV2-derived ITR flanking an AAV2-derived packaging sequence and a nucleic acid encoding a therapeutic protein) in an AAV2-derived capsid; vectors comprising an AAV4-derived genome in an AAV4-derived capsid; vectors comprising an AAV6-derived genome in an AAV6-derived capsid; vectors comprising an AAV8-derived genome in an AAV8-derived capsid; vectors comprising an AAV9-derived genome in an AAV9-derived capsid.

In another particular embodiment, the AAV vector is a pseudotyped AAV vector, i.e. the vector comprises sequences or components originating from at least two distinct AAV serotypes. In a particular embodiment, the pseudotyped AAV vector comprises an AAV genome derived from one AAV serotype (for example AAV2), and a capsid derived at least in part from a distinct AAV serotype. Specific examples of such pseudotyped AAV vectors include, without limitation, vectors comprising a genome derived from any AAV serotype (for example from AAV1 to AAV11), in an AAV6, AAV8 or AAV9-derived capsid. Preferably, the scAAV genome is derived from an AAV2 genome. Specific examples of such pseudotyped scAAV whose genome is derived from an AAV2 genome include, without limitation, vectors comprising an AAV6, AAV8 or AAV9 derived capsid. In another particular embodiment, the pseudotyped scAAV vector comprises a genome derived from any of the above mentioned AAV serotype (for example from serotypes 1-11), in an AAV9-derived capsid. In a preferred embodiment of the invention, the scAAV vector is a vector comprising an AAV2-derived genome in an AAV9-derived capsid (also referred to as scAAV2/9).

In a further particular embodiment, which may be combined with any of the above embodiments, the scAAV vector may comprise a modified capsid, including proteins or peptides of non viral origin or structurally modified, to alter the tropism of the vector (capsid mutants or "hybrid" serotypes). Retargeting of these vectors could be based on different types of modification such as transcapsidation, adsorption of specific antibodies to capsid surface (including a ligand of a particular receptor, or a receptor of a particular ligand, to target the vector towards cell type(s) expressing said receptor or ligand, respectively), mosaic capsid, chimeric capsid (Vivian W. Choi, Curr Gene Ther. 2005).

As discussed above, the AAV-derived genome comprises a therapeutic gene encoding in particular a therapeutic protein. Typically in this embodiment, the nucleic acid also comprises regulatory sequences allowing expression and, preferably, secretion of the encoded protein, such as e.g., a promoter, enhancer, polyadenylation signal, internal ribosome entry sites (IRES), sequences encoding protein transduction domains (PTD), and the like. In this regard, the nucleic acid most preferably comprises a promoter region, operably linked to the coding sequence, to cause or improve expression of the therapeutic protein in infected cells. Such a promoter may be ubiquitous, tissue-specific, strong, weak, regulated, chimeric, inducible, etc., to allow efficient and suitable production of the protein in the infected tissue. The promoter may be homologous to the encoded protein, or heterologous, including cellular, viral, fungal, plant or synthetic promoters. Most preferred promoters for use in the present invention shall be functional in cells or the retina, more preferably in photoreceptor or ganglion cells of the retina or in cells of the RPE. Examples of such regulated promoters include, without limitation, Tet on/off element-containing promoters, rapamycin-inducible promoters and metallothionein promoters. Examples of ubiquitous promoters include viral promoters, particularly the CMV promoter, the RSV promoter, the SV40 promoter, etc. and cellular promoters such as the PGK (phosphoglycerate kinase) promoter. The promoters may also be neurospecific promoters such as the Synapsin or the NSE (Neuron Specific Enolase) promoters (or NRSE (Neuron restrictive silencer element) sequences placed upstream from the ubiquitous PGK promoter), or promoters specific for various retinal cell types such as the RPE65, the VMD2, the Rhodopsin or the cone arrestin promoters.

In case the therapeutic gene encodes a therapeutic RNA, classical RNA polymerase pol III promoters may be used for shRNA expression (for example, human or murine H1 or U6 promoters). Ribozymes and antisense sequences are usually expressed from standard polymerase II promoters. As is known in the art, inducible expression cassettes can also be adapted for AAV-mediated shRNA expression.

The nucleic acid may also comprise target sequences for miRNAs achieving suppression of transgene expression in non-desired cells. For example, suppression of expression in the hematopoietic lineages ("de-targeting") enables stable gene transfer in the transduced cells by reducing the incidence and the extent of the transgene-specific immune response (Brown B D, Nature Medicine 2008).

In a particular embodiment, the nucleic acid comprises a leader sequence allowing secretion of the encoded protein. Fusion of the transgene of interest with a sequence encoding a secretion signal peptide (usually located at the N-terminal end of secreted polypeptides) will allow the production of the therapeutic protein in a form that can be secreted from the transduced cells. Examples of such signal peptides include the albumin, the β-glucuronidase, the alkaline protease or the fibronectin secretory signal peptides.

According to another specific embodiment, the transgene is fused with PTD sequences, such as the Tat or VP22 sequences, in order to cause or improve secretion of the therapeutic protein from the transduced cells and re-uptake by neighbour ones.

In a particular embodiment the nucleic acid comprises, operably linked, a promoter and a leader sequence, to allow expression and secretion of the encoded protein.

In a further particular embodiment, the nucleic acid comprises, operably linked, a promoter, a leader sequence and a PTD sequence, to allow expression and secretion of the encoded protein.

In a most preferred embodiment, the promoter is specific or functional in cells of the retina, in particular in photoreceptor or ganglion cells of the retina or in the RPE, i.e., allows (preferential) expression of the transgene in said cells.

In a particular embodiment the nucleic acid comprises an intron (for example a chimeric intron) to enhance expression of the mRNA and encoded protein. In a specific variant of this embodiment, the invention relates to a scAAV9 (or scAAV2/9) vector comprising a gene of interest (i.e. a transgene, for example one of the therapeutic genes described below) under the control of a promoter (preferably a promoter that is specific or functional in cells of the retina), wherein an heterologous or chimeric intron is present between said promoter and said gene of interest. Insertion of heterologous introns between a promoter and a transgene has been reported to improve expression (Palmiter et al., 1991, PNAS, 88, 478-482). Chimeric introns are available commercially, for example from Promega. An illustrative chimeric intron that can be used in the vector of the invention is composed of the 5' donor splice site of the human β-globin intron 1 and the branch point, and the 3'-acceptor splice site from an intron derived from the immunoglobulin gene heavy chain variable region.

As discussed above, the scAAV vectors may be produced by techniques known per se in the art, as further illustrated in the examples.

Systemic Administration

The invention is based on the unexpected discovery that effective and widespread expression of genes into cells of the retina can be achieved through systemic administration of AAV vectors. Such systemic administration includes, without limitation, any administration route which does not imply direct injection into the retina, such as subretinal or intravitreal injection. More particularly, the systemic administration includes a systemic injection of the scAAV vector, such as intramuscular (i.m.), intravascular, i.e. intra-arterial (i.a.) or intravenous (i.v.), intraperitoneal (i.p.), sub-cutaneous or transdermic injections. Peripheral administration also includes oral administration of AAV vectors (WO96/40954), delivery using implants (WO01/91803), or administration by instillation through the respiratory system (for example by the intranasal route), e.g., using sprays, aerosols or any other appropriate formulations. Most preferred systemic administration include the systemic injection of the scAAV vector, most preferably via an i.m., i.p., i.a. or i.v. injection. Most preferably, the scAAV vector is administered via an i.v. injection.

The scAAV vectors are typically administered in a "therapeutically-effective" amount, i.e., an amount that is sufficient to alleviate (e.g., decrease, reduce) at least one of the symptoms associated with the disease state, or to provide improvement in the condition of the subject. It should be pointed out that repeated administrations may be performed, if required, using either the same or different systemic administration routes and/or the same or distinct scAAV serotypes. Alternatively, a single administration of the scAAV may also be performed.

The doses of scAAV vectors may be easily adapted by the skilled artisan, e.g., depending on the disease condition, the subject (for example, according to his weight, metabolism, etc.), the treatment schedule, etc. A preferred effective dose within the context of this invention is a dose allowing an optimal transduction of the cells of the retina (photoreceptor or ganglion cells or cells of the RPE). Typically, from $10^9$ to $10^{14}$ viral genomes (transducing units) are administered per dose in mice, preferably from about $10^{11}$ to $10^{13}$. Typically, the doses of AAV vectors to be administered in humans may range from $10^{11}$ to $10^{17}$ viral genomes, preferably from $10^{13}$ to $10^{16}$, most preferably from $10^{14}$ to $10^{15}$.

The scAAV vector may be administered in any suitable form, either as a liquid solution or suspension, as a solid form suitable for solution or suspension in liquid prior to injection, as a gel or as an emulsion. The scAAV vectors are typically formulated with any appropriate and pharmaceutically acceptable excipient, carrier, adjuvant, diluent, etc. For injection, the excipient may be a liquid, isotonic solution, buffer, such as sterile and pyrogen-free water or a sterile and pyrogen-free phosphate-buffered saline solution. For inhalation, the excipient may be in particulate form.

Eye/Retina Diseases

The invention shows, for the first time, that a single systemic administration of scAAV vectors causes substantial transduction of cells of both eyes. In particular, transduction of the ciliary bodies, the nerve fiber layer, the optic nerve, and the different cell layers of the retina has been observed.

In particular, the invention shows that scAAV vectors (in particular scAAV9 vectors, more particularly scAAV2/9) vectors administered systemically cause substantial transduction of cells of the retina, particularly of photoreceptor cells, ganglion cells, glial cells (in particular Müller cells), inner nuclear layer (INL) cells (including bipolar cells, horizontal cells, and amacrine cells), or cells of the retinal pigmented epithelium (RPE), probably by crossing the blood retina barrier. The results presented herein show that transduction is effective from the innermost layer of the retina to the RPE, thereby providing a widespread gene delivery into the retina.

The invention thus provides a method for delivering a gene to each of these specific cell types, comprising the systemic administration of a scAAV vector (in particular a scAAV9, more particularly a scAAV2/9 vector) carrying said gene in its genome.

The invention may thus be used to treat a variety of disorders through delivery of a therapeutic product into the above cells, in particular into cells of the retina. The therapeutic product may be any protein, peptide or RNA that may alleviate or reduce symptoms that result from an absence, defect or overexpression of a protein in a cell of a subject or that otherwise confers a benefit to a subject (for example by producing from the retina a secreted trophic factor which may treat a pathological state resulting from cells remote from the retina). One skilled in the art knows, by its knowledge of the scientific literature in his field, which are the genes that may be more appropriate to include in the scAAV vector of the invention to treat a specific disease. Examples of therapeutic proteins include growth factors, cytokines, hormones, neurotransmitters, enzymes, anti-apoptotic factors, angiogenic or anti-angiogenic factors, and any protein known to be mutated in pathological disorders such as Retinitis pigmentosa (for example the protein coded by retinal pigment epithelium-specific protein 65 kDa (RPE65) or ATP-binding cassette, sub-family A (ABC1), member 4 (ABCA4) gene) and Leber congenital amaurosis ((for example the protein coded by retinal pigment epithelium-specific protein 65 kDa (RPE65) or guanylate cyclase 2D, membrane (retina-specific) (GUCY2D) gene).

The great therapeutic potential of bipolar cells targeting has been demonstrated by restoration of vision in blind mice following expression of light-activated channels in ON bipolar cells (Lagali et al, 2008, Nature Neuroscience, 11, 6, 667-675). Therefore, a particular embodiment of the invention relates to targeting of bipolar cells with a scAAV vector (in particular scAAV2/9), comprising a gene intended to restore vision, in particular the channel rhodopsin-2 gene (ChR2).

The invention further more particularly relates to methods and uses as defined above, comprising administering a scAAV vector (in particular scAAV2/9), comprising a gene intended to treat Leber's congenital amaurosis or retinitis pigmentosa, for example the RPE65 gene.

The invention relates also to a scAAV vector, in particular a scAAV9 or scAAV2/9 vector, encoding at least one of the above therapeutic proteins.

Examples of therapeutic RNA include antisense RNA or sRNA (or shRNA) or microRNA (miRNA) having a therapeutic interest in any of the diseases mentioned herein below (such as VEGF mRNA-targeting sRNA or miRNA). The invention thus relates to a scAAV vector, in particular a scAAV9 or scAAV2/9 vector, encoding a sRNA or a miRNA having a therapeutic interest in an ocular disease, such a the diseases mentioned below. In a particular embodiment, the invention relates to a scAAV vector, in particular a scAAV9 or scAAV2/9 vector, encoding a VEGF mRNA-targeting sRNA (or sh-RNA) or miRNA.

Depending on the therapeutic product, the invention can be used to treat various diseases of the eye, including any disease which may be treated or prevented by expressing therapeutic proteins into, or from, cells of the retina. Such diseases include both inherited (for example Leber's congenital amaurosis) and sporadic (for example diabetic retinopathy) eye disorders, including in particular disorders of the choroid and retina. Some of these diseases include retinitis pigmentosa, macular degeneration, cone-rod dystrophy, retinal detachment, retina degeneration, hypertensive retinopathy, retinoblastoma, Leber's congenital amaurosis, macular edema, Birdshot chorioretinopathy, vitelliform macular dystrophy, glaucoma, disorders of the vitreous body and globe, etc. The present invention also provides means of treating other disorders of the eye (by gene transfer of a secreted therapeutic protein) including disorders of sclera, cornea, iris and ciliary body, disorders of optic nerve and visual pathways (ex: Leber's hereditary optic neuropathy), disorders of ocular muscles, etc.

The invention can also be used to infect cells which will produce a secreted product. In particular, a scAAV (in particular scAAV9, more particularly scAAV2/9) comprising a gene of interest encoding a secreted protein can be used to infect the above described cells, in particular cells of the ciliary body. After infection, these cells will release the secreted product (in particular a secreted protein) in the intraocular tissue of the eye and thereby allow the treatment of a wide range of ocular diseases. For example, the invention provides the treatment of an ocular disease by systemically administering a scAAV vector (e.g. a scAAV9 or scAAV2/9 vector) comprising a gene encoding a secreted anti-VEGF antibody. The invention thus also relates to a scAAV vector, in particular a scAAV9 or scAAV2/9 vector encoding an anti-VEGF antibody.

The invention may be used in any mammalian, particularly in human subjects, including adults, for preventive or curative treatment.

The invention can also be used in diagnostic methods, to detect the status, activity or growth of cells or sub-tissue sections of the retina in mammalian subjects. For such indications, the vector typically comprises a detectable gene (fluorescent, luminescent, etc.) and is used as a marker.

The invention can also be used in animal subjects, e.g., to assist in the research of candidate drugs for treating disorders of the eye, in particular of the retina, and/or to understand the mechanisms of growth, differentiation, activity, etc., of cells of the retina.

Further aspects and advantages of the present inventions will be disclosed in the following experimental section, which shall be considered as illustrative only, and not limiting the scope of this application.

EXAMPLES

Materials and Methods

Animals

Adult C57Bl/6 mice (6 to 8 weeks old, female, 16 mice) were purchased from Charles River Laboratories (Les Oncins, France). All animal experiments were carried out according to European guidelines for the care and use of experimental animals and were approved by the regional ethics committee (CREEA).

Vectors

AAV vectors express green fluorescent protein (GFP) or mouse secreted alkaline phosphatase (mSEAP) under the control of the cytomegalovirus immediate early (CMV) promoter. Production of serotype 9 AAV has been previously described (Duque et al., 2009). Briefly, pseudotyped AAV2/9 vectors were generated by packaging AAV2-based recombinant single stranded (ss) or self-complementary (sc) genomes into AAV9 capsids. The vectors were produced by helper virus-free, three-plasmid transfection, in HEK293 cells, using (1) the adenovirus helper plasmid (pXX6-80) (2) the AAV packaging plasmid encoding the rep2 and cap1 or 9 genes (pLTRCO2 for AAV1 and p5E18-VD2/9 for AAV9) (3) the AAV2 shuttle plasmid containing the gene encoding GFP (under control of the cytomegalovirus immediate early (CMV IE) promoter) in a sc genome or the gene encoding mSEAP (murine secreted alkaline phosphatase) in a ss or sc genome. The sc genome containing plasmids were constructed by deleting the D sequence and the terminal resolution site (trs) from one of the inverted terminal repeats. Recombinant vectors (rAAV) were purified by double-CsCl ultracentrifugation followed by dialysis against phosphate-buffered saline (five buffer changes, 3 hours per round of dialysis). Physical particles were quantified by real-time PCR for vectors injected into mice and by dot blot hybridization for vectors injected into kittens. Vector titers were expressed as viral genomes per milliliter (vg/ml).

In Vivo rAAV Injections 12 adult mice were injected into the tail vein with the ssAAV1-mSEAP, scAAV1-mSEAP, ssAAV9-mSEAP and scAAV9-mSEAP (4 mice with $3 \times 10^{11}$ vg and 8 mice with $10^{12}$ vg per mouse).

Four adult mice (6 weeks old) were injected into the tail vein with $2 \times 10^{12}$ vg scAAV9-GFP in a volume of 500 µl. A 30 gauge needle attached to a 1 ml syringe was inserted in the tail vein and 500 µl of the viral solution was injected in approximately 30 seconds.

mSEAP Quantification Assay

Frozen tissues were lysed in 700 µl of nuclei lysis Buffer included in the Wizard genomic DNA extraction kit (Promega corporation) containing a cocktail of protease inhibitor (Sigma-Aldrich). The tissues were first homogenized for 30 sec with an Ultra-Turrax and then submitted to three successive homogenizations to achieve complete lysis. Cells membranes and debris were pelleted by centrifugation 2 minutes at 10,000 g at 4° C. mSEAP activity was measured in the supernatant using a chemiluminescent assay. Briefly, endogenous alkaline phosphatase was heat inactivated 5 minutes at 65° C. and the heat resistant mSEAP was measured by addition of the reaction buffer and CPSD chemiluminescent substrate, according to the manufacturer's instructions (Tropix, Applied Biosystems). Chemiluminescence was quantified using a luminometer (Perkin Elmer). Expression/activity levels are expressed as ng of mSEAP per lysate according to a standard curve of purified human placental alkaline phosphatase and are standardized per µg of protein using a nano-orange protein quantitation Assay® (Invitrogen).

Vector Genome Copy Number Quantification

Genomic DNA extraction (Wizard genomic DNA extraction kit, Promega) was performed on the eye lysates. Viral genomes were quantified by a real time PCR assay using primers and probes corresponding to the inverted terminal repeat region (ITR) of the AAV vector genome. The sequences used for the primer pairs were AAV-Fw 5'-CTCCATCACTAGGGGTTCCTTG-3' (SEQ ID NO:1), AAV-Rev 5'-GTAGATAAGTAGCATGGC-3' (SEQ ID NO:2) and for the MGB probes was AAV-p 5'-TAGTTAATGATTAACCCAAV-3' (SEQ ID NO:3). Data are expressed as genome copy number per cell using the titin gene amplification reaction for normalization per cell. The primer pairs and Taqman probes for titin amplification were: Titin-Fw 5'-AAAACGAGCAGTGACGTGAGC-3' (SEQ ID NO:4), Titin-Rev 5'-TTCAGTCATGCTAGCGC-3' (SEQ ID NO:5), Titin Vic/TAMRA probe 5'-TGCACGGAAGCGTCTCGTCTCAGTC-3' (SEQ ID NO:6). For analysis, 72 ng of genomic DNA was used as template. Dilutions of the rAAV vector plasmid were used to generate a standard curve for determination of vector genome copies. PCR was carried out using Applied biosystems 7700 and data were analyzed with Sequence Detection System (Applied Biosystems).

Histological Analysis

The mice were anesthetized (10 mg/kg xylazine, 100 mg/kg ketamine) 30 days after injection and perfused intracardially with 0.1 M phosphate-buffered saline (PBS), followed by 4% paraformaldehyde (PFA) in PBS. The eyes were removed and post-fixed by overnight incubation in 4% PFA. They were then incubated overnight at 4° C. in 15% sucrose, frozen in cold isopentane (−50° C.) and cut on a cryostat (14 µm sections).

GFP Immunofluorescence

The cryosections were incubated for 1 h with 10% goat serum and 0.4% Triton X-100 in PBS and then overnight with the rabbit polyclonal anti-GFP antibody (Abcam, 1:800). Sections were washed in PBS and then incubated for 1 h at room temperature with biotinylated anti-rabbit IgG (Vector Laboratories, 1:200). GFP immunofluorescence was detected by incubation with streptavidin-A488 (Molecular Probes, 1:200). Sections were washed in PBS, mounted in Fluoromount-G and observed by confocal microscopy (Leica, laser emission: 488 nm, green).

Further Histological Processing

The following protocol has further been used for histological analysis of the eyes of treated animals, in particular for double-immunofluorescence analysis.

Mice were deeply anesthetized with 10 mg·kg-1 Xylazine and 100 mg·g-1 Ketamine and trans-cardially perfused with 0.1 M phosphate-buffered saline (PBS) followed by ice-cold 4% paraformaldehyde in PBS. After enucleation, the eyes were post-fixed by overnight incubation in the same fixative, cryoprotected overnight in 15% sucrose in PBS, frozen in cold isopentane (−50° C.) and cut on a cryostat in 14 µm-thick sections, which were stored at −80° C. until further processing. For immunofluorescence labeling, sections were rinsed twice in PBS, blocked for one hour in PBS containing 10% normal goat serum (NGS) and 0.2% triton X-100, incubated overnight at 4° C. with primary antibodies in PBS containing 1% NGS and 0.2% triton X-100. Anti-GFP antibody (1:800; Abcam, Cambridge, UK), anti-Brn-3a antibody (1:1'000; Millipore, Billerica Mass., USA), and anti-Chx10 antibody (1:300; Santa Cruz Biotechnology, Santa Cruz, Calif., USA) were used. Sections were then rinsed in PBS, incubated with fluorescently-labeled secondary antibodies (Alexa-Fluor conjugates, 1:1'000; Invitrogen, Cergy-Pontoise, France), labeled with 4',6'-diamidino-2-phenylindol (dapi), and mounted under coverslips with mowiol 4-88 reagent (Sigma-Aldrich, Lyon, France) before examination on a DM6000-B epifluorescence microscope (Leica Microsystèmes, Nanterre, France). Brn-3a and GFP positive cells were manually counted using the 20× objective of the microscope.

Results

Vector Genome Copy Number Quantification

To analyze the efficiency of different AAV vectors for systemic gene transfer in the adult mouse retina, ssAAV1, scAAV1, ssAAV9 and scAAV9 vectors encoding mSEAP were injected into the tail vein of 12 adult mice (2 mice in each group were injected with $3 \times 10^{11}$ vg, and 1 mouse per group with $1 \times 10^{12}$ vg).

The number of vg particles per cell was evaluated in eye tissue samples from all AAV-injected mice. In general, scAAVs were superior for mediating cell transduction than ssAAVs, whatever the serotype of the capsid is. The scAAV9 vector even mediated a higher number of vg particles per cell than the scAAV1 in the injected mice (FIG. 1A).

These results clearly show the superiority of the scAAV, and most particularly of the scAAV9, for I.V. eye transduction.

Quantification of mSEAP Activity

To verify the efficiency of scAAV9 for systemic eye transduction, mSEAP activity was analyzed by biochemical analysis on the tissue samples from the ssAAV9 and scAAV9 injected mice.

Again, the eyes from mice injected with the scAAV9 vector appeared highly transduced as compared to those of mice injected with the single-strand vector (FIG. 1B).

GFP Immunofluorescence

In order to analyse transgene distribution in the retina of mice IV injected with the scAAV9 vectors, 4 adult mice were injected into the tail vein with $2 \times 10^{12}$ vg scAAV9-GFP.

A GFP immunofluorescence analysis performed on histological sections from treated mice revealed a substantial GFP expression in several retina layers (FIGS. 2a,b), including the ganglion cell layer (GCL) (FIGS. 2a-d), the inner nuclear layer (INL) (FIGS. a,b,e), the photoreceptor cells (FIG. 2f), and the RPE (FIG. 2a). Expression was most intense in the ganglion cell layer (FIGS. 2c,d). GFP expression was also found in the optic nerve (axons of the ganglion cells) (FIGS. 3a,b), and was particularly intense in the ciliary bodies (FIGS. 3c,d).

Transgene expression appeared most intense in the areas close to the ciliary bodies, suggesting that the vectors, concentrated in these non-retinal structures, could diffuse to the retinal cell layers. In conclusion, IV administration of scAAV9-GFP in adult mice resulted in a widespread transduction of retinal and non retinal cells.

The inventors have further described their results as follows and provide double-immunofluorescence experiments.

To address the issue of vector biodistribution in neural tissue, AAV constructions expressing the reporter gene mSEAP (secreted form of the murine alkaline phosphatase) under the transcriptional control of the CMV promoter were used. scAAV9 and ssAAV9 were compared for their efficiency to transduce ocular tissue. Animals received an intravenous injection of 10e12 vector genome of either ssAAV9 or scAAV9 encoding the mSEAP reporter gene. Four weeks after injections, the eyes were enucleated for quantification of AAV vector genome and mSEAP activity on whole eyes. Normalization of the real-time PCR experiments by the endogenous gene Titin demonstrated a vector genome copy number per cell of 0.010+/−0.003 for ssAAV injected animals (n=3), showing that ssAAV9 is able to reach ocular tissues after systemic delivery. This parameter increased up to 0.318+/−0.198 in scAAV injected animals (n=3), showing that self-complementary AAV vectors offer a gain in transduction compared to their single strand counterpart. To assess for transgene expression, we quantified the mSEAP activity in the ocular tissue lysates. An activity of 1.7+/−0.9 pg of mSEAP per mg of protein has been measured for ssAAV9 injected mice. In accordance to the increased vector genome copy number per cell, the mSEAP activity was 6 fold higher after scAAV9 administration, leading to 10.1+/−3.4 pg of mSEAP per mg of protein in treated animals.

Based on these results, we focused our study on scAAV9, and analyzed the expression pattern of the GFP protein in the retina of mice intravenously injected with scAAV9 vectors expressing GFP under the transcriptional control of the CMVie promoter. Eight weeks-old mice were injected into the tail vein with scAAV9-GFP at a dose of $2.10^{12}$ vector genome per animal. Four weeks after injection GFP expression was detected by immunofluorescence labeling on cryostat sections. GFP-expressing cells were detected in all layers of the retina (FIG. 4). Based on cell morphology, GFP expression was found in photoreceptors (FIGS. 4C, D, G and H), in RPE cells (FIGS. 4E, H), in Müller cells, in inner nuclear layer cells (FIGS. 4C-H), in the nerve fiber layer and the optic nerve (axonal fibers from the ganglion cells) (FIGS. 4I,J). Notably, the retinal ganglion cell (RGC) layer appeared mostly transduced, displaying numerous GFP-positive cell bodies (FIGS. 4A-H).

To precisely determine the phenotype of the GFP-expressing cells, we performed double-immunostaining analyses using antibodies that specifically recognized different retinal cell types (such as Brn-3a, a POU Domain transcription factor which is specifically expressed in the nuclei of retinal ganglion cells (RGC) (Nadal-Nicolas et al., 2009) or Chx10, a transcription factor which is expressed specifically in the nucleus of bipolar cells (Liu et al., 1994)).

GFP/Brn-3a double-immunofluorescence demonstrated that a large proportion of GFP-positive cells in the retina were ganglion cells (FIG. 5 A-C). Moreover, GFP/Chx10 co-staining analyses showed that some GFP transduced cells in the inner nuclear layer of the scAAV9 injected animals were bipolar cells (FIGS. 5D-F).

We further quantified gene transfer efficiency in the ganglion cells in the RGC layer on three transverse sections located at the level of the optic nerve and counted the GFP positive cells, the number of Brn-3a positive cells and the number of cells co-expressing both markers. Our results showed that systemic scAAV9-GFP delivery in adult mice led to the transduction of an average of 222.4+/−20.1 GFP-positive cells per retinal section in the RCG layer. Among them 122.4+/−9.1 were double-labeled with Brn-3a, demonstrating 45%+/−3 of the transduced RGC cells were ganglion cells (mean+/−SD of six different eyes).

Altogether, these results show the efficiency of scAAV to transduce the retina cells following systemic delivery in adult mice, suggesting efficient crossing of the blood-retina barrier. Diffusion of the vector from highly transduced non-retinal structures such as the ciliary bodies could also be suggested (FIG. 3).

In contrast to the previous experiments from Bostick and collaborators (Bostick et al., 2007), we demonstrated that IV scAAV injection was efficient to deliver transgenes in the retina of adult mice, in which the blood retina barrier is mature. The different transfected cell types were identified either by morphological and location criteria, or by double-immunofluorescence analysis. Efficient gene transfer to the adult retina is highly valuable for future clinical application in symptomatic patients.

The invention claimed is:

1. A method of treating a disorder of the eye, the method comprising the systemic administration of a double stranded self-complementary AAV (scAAV) vector comprising a therapeutic gene to a subject having the disorder of the eye, and wherein said method comprises delivery of the therapeutic gene to photoreceptor cells, glial cells, cells of the retinal pigmented epithelium (RPE) or cells of the ciliary body.

2. The method according to claim 1, said method comprising delivery of the therapeutic gene to the photoreceptor cells, the glial cells or the cells of the RPE.

3. The method according to claim 1, wherein said method transduces the cells of the ciliary body.

4. The method according to claim 1, wherein said systemic administration is an intraperitoneal (i.p.), intramuscular (i.m.), intra-arterial or intravenous (i.v.) injection.

5. The method according to claim 1, wherein said scAAV vector is a human serotype AAV vector.

6. The method according to claim 1, wherein the scAAV vector comprises an AAV9-derived capsid.

7. The method according to claim 1, wherein the scAAV vector is a pseudotyped scAAV vector.

8. The method according to claim 1, wherein the scAAV vector comprises a replication defective scAAV genome lacking functional Rep and Cap coding viral sequences.

9. The method according to claim 1, wherein the therapeutic gene encodes a therapeutic RNA or a therapeutic protein known to be mutated or deficient in the disorder of the eye.

10. The method according to claim 1, wherein the disorder of the eye is selected from inherited and sporadic eye disorders, diabetic retinopathy, disorders of the choroid and retina, retinitis pigmentosa, macular degeneration, cone-rod dystrophy, retinal detachment, hypertensive retinopathy, diabetic retinopathy, retinoblastoma, macular edema, Birdshot chorioretinopathy, vitelliform macular dystrophy, glaucoma, optic neuropathy, disorders of the vitreous body and globe, disorders of sclera, cornea, iris and ciliary body, disorders of optic nerve and visual pathways or disorders of ocular muscles.

11. The method according to claim 1, wherein the double stranded scAAV vector comprising the therapeutic gene is administered in the form of a liquid solution, a suspension, a gel, or an emulsion.

12. The method according to claim 11, wherein the liquid solution, the suspension, the gel, or the emulsion is a non-liposomal solution, suspension, gel or emulsion.

13. The method according to claim 11, wherein the liquid solution, the suspension, the gel, or the emulsion is free from liposomes and/or antibodies against the receptor present on the blood-retina-barrier and/or the plasma membrane of the cells in the retina and/or other structures of the eye.

14. A method of treating a disorder of the eye, the method comprising the systemic administration of a composition consisting of a double stranded scAAV vector and a sterile isotonic solution or buffer to a subject having the disorder of the eye, wherein the scAAV vector comprises a therapeutic gene of interest, and wherein said method comprises delivery of the therapeutic gene to photoreceptor cells, glial cells, cells of the RPE or cells of the ciliary body.

15. The method according to claim 14, wherein said sterile isotonic solution or buffer is a saline buffer or isotonic saline solution.

16. The method according to claim 15, wherein said sterile isotonic solution or buffer is phosphate buffered saline.

17. The method according to claim 2, said method comprising delivery of the therapeutic gene to cells of the RPE.

18. The method according to claim 2, said method comprising delivery of the therapeutic gene to photoreceptor cells.

19. A method of treating a disorder of the eye, the method comprising systemic administration of a double stranded self-complementary AAV (scAAV) vector comprising a therapeutic gene to an adult subject having the disorder of the eye, wherein said method comprises delivery of the therapeutic gene to retinal cells of the adult subject.

20. The method according to claim 19, said method comprising delivery of the therapeutic gene to photoreceptor cells, ganglion cells, glial cells, inner nuclear layer (INL) cells, or cells of the RPE.

21. The method according to claim 19, wherein said method transduces cells of the ciliary body, cells of the nerve fiber layer or the cells of the optic nerve.

22. The method according to claim 20, said method comprising delivery of the therapeutic gene to cells of the RPE.

23. The method according to claim 21, wherein said method transduces cells of the ciliary body.

24. The method according to claim 20, said method comprising delivery of the therapeutic gene to photoreceptor cells.

25. The method according to claim 19, wherein the scAAV is scAAV9.

* * * * *